(12) United States Patent
Bernard et al.

(10) Patent No.: US 6,319,901 B1
(45) Date of Patent: *Nov. 20, 2001

(54) METHODS FOR PROLONGING CELL MEMBRANE PERMEABILITY

(75) Inventors: Robert M. Bernard, Rancho Santa Fe; Andrew W. Hannaman, San Diego; Silvia Sfiligoi, Del Mar, all of CA (US)

(73) Assignee: Ichor Medical Systems, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/173,303

(22) Filed: Oct. 15, 1998

(51) Int. Cl.[7] .................. A61K 31/355; A61K 31/56; A61K 31/573; A61K 38/08; A61N 1/30
(52) U.S. Cl. .................. 514/16; 514/171; 514/177; 514/179; 514/180; 514/458; 604/20

(58) Field of Search .................. 424/130.1; 514/2, 514/44, 8, 16, 171, 179, 180, 177, 458, 772, 773; 604/20; 607/115, 148

(56) References Cited

U.S. PATENT DOCUMENTS

| | | | | |
|---|---|---|---|---|
| 5,215,520 | * | 6/1993 | Shroot et al. | 604/20 |
| 5,334,138 | * | 8/1994 | Sage, Jr. et al. | 604/20 |
| 5,693,010 | * | 12/1997 | Ledger et al. | 604/20 |
| 5,911,223 | * | 6/1999 | Weaver et al. | 604/20 |

* cited by examiner

Primary Examiner—Jeffrey E. Russel
(74) Attorney, Agent, or Firm—James C. Weseman, Esq.; The Law Offices of James C. Weseman

(57) ABSTRACT

Methods for improving the efficiency of electroporation protocols as well as methods to enhance the permeabilized state, in order to improve the intracellular delivery of therapeutic substances, involve the use of at least one agent which is capable of prolonging the permeability of the cell membranes in the tissue exposed to an electroporation-inducing electrical field.

16 Claims, 6 Drawing Sheets

|←——— 3.0 cm ———→|

|←——— 3.0 cm ———→|

METHODS FOR PROLONGING CELL MEMBRANE PERMEABILITY

TECHNICAL FIELD

The present invention relates to the delivery of substances across cell membranes and, more particularly, to the use of electroporation as a means for the intracellular delivery of therapeutic substances.

BACKGROUND OF THE INVENTION

The application of brief, high intensity electrical pulses has long been known to cause a transient state of permeability in the membranes of cells. It has been demonstrated in vitro that the intracellular concentration of normally impermeant substances, such as dyes (Mir et al. *Exp. Cell Research* 175: 15–25, (1988)), genes ((Chang, D. et al. in "Guide to Electroporation and Electrofusion" D. Chang ed., Academic Press, San Diego, pp. 1–6 (1992)), drugs (Poddevin et al., *Biochem Pharmacol* 42 Suppl: S67–S75 (1991)), and proteins (Mouneimne et al., *Biochim et Biophys Acta* 1027:53–58 (1990)) can be dramatically increased while cells exhibit this transient permeability. This process, known as electroporation, has also been applied in vivo to increase the permeability of cells in tissue.

Many studies have reported a substantial improvement in the cytotoxicity of certain membrane-limited chemotherapeutic drugs when used in conjunction with electroporation. Animal studies (Mir et al., *Eur J Cancer* 27:68–72 (1991), Belehradek et al., *Eur J Cancer* 27:73–76 (1991), Heller et al., *Bioelectrochem Bioenerg* 36:83–87 (1995), Jaroszeski et al., *Biochim et Biophys Acta* 1334:15–18 (1997)) and early human trials (Domenge et al., *Cancer* 77:956–963 (1996), Heller et al., *Cancer* 77:964–966 (1996)) have indicated that electroporation therapy shows great promise as a treatment for solid tumors because the chemotherapeutic drugs delivered by this technique can be made very effective while minimizing side effects.

While the initial development of electroporation technology has been in the area of drug delivery, another application of electroporation therapy currently being studied involves the use of gene therapy. Although gene therapies are currently being developed for the treatment of many diseases, including cancer, diabetes, heart disease, and arthritis, a safe and reliable technique for their delivery has yet to be developed for clinical use. Several studies (Heller et al., *FEBS Letters* 389:225–228 (1996), Rols et al., *Nature Biotechnology* 16:168–171 (1998), Harimoto et al., *Brit. J. Urology* 81:870–874 (1998)) demonstrate that transfection and expression of marker genes, such as luciferase and β-galactosidase, can be improved in vivo by the application of electrical pulses to the tissue of a targeted area. These results suggest that electroporation may provide a feasible method for the transfection of genetic material into living cells in tissue.

The use of electroporation therapy for the transmembrane delivery of therapeutic substances is dependent on achieving two necessary and sufficient conditions in the region to be treated: (I) Adequate concentration of therapeutic substance must be present in the extracellular space, and (II) Threshold level electrical fields must be generated throughout the target tissue. While a significant amount of research has been performed demonstrating the utility of electroporation in the treatment of various animal and human tumor models (Heller et al. (1995), Hofmann et al., *IEEE Eng Med and Biol,* 124–132 (November/December 1996), Jaroszeski et al. (1997)), there is limited understanding regarding the best methods for the clinical application of electroporation therapy.

In the field of cancer treatment, delivery of therapeutic substances is made more difficult by the anatomical characteristics of solid tumors such as nonuniform vasculature and high interstitial pressure. These properties make it difficult to achieve uniform, high concentrations of therapeutic substances within the tumor (Jain, R., *Scientific American* 271(1):58–65 (1994)). The tortuous, nonuniform vasculature prevents blood borne substances from reaching all parts of the tumor. Due to high interstitial pressures, maintaining the necessary concentrations of drug within the tumor is also difficult, because this pressure gradient causes substances to be forced back into the vasculature or carried by convection to the exterior of the tumor. The nature of current chemotherapeutic drugs also limits their effectiveness. While administration of drugs into the vasculature provides excellent distribution, systemic dosages of therapeutic substances are often limited by their toxic side effects. Therefore, a higher concentration of therapeutic substance cannot be achieved simply by increasing the systemic dosage, without serious risk of harm to the patient.

Given the problematic nature of delivering high levels of therapeutic substance to solid tumors, electroporation therapy seems well suited to the treatment of these cancers. However, methods must be employed to ensure that sufficient levels of therapeutic substance are present in the interstitial space when the permeabilizing pulses are delivered. Because membrane permeability occurs as a result of exposing a cell to threshold level electric field strengths, an effective electroporation therapy is dependent on propagating these fields throughout a target region of tissue and allowing sufficient concentrations of the desired substances to accumulate intracellularly.

Thus, it is considered desirable to provide a means for increasing the amount of therapeutic substance which accumulates in the cells of electroporated tissue.

DISCLOSURE OF THE INVENTION

The present invention provides methods to facilitate the intracellular delivery of substances via electroporation. In particular, these methods can be applied to improve the benefit derived from the application of electroporation therapy to diseased tissue.

In one aspect, the invention provides a method for delivering a therapeutic substance to a predetermined location in a patient comprising providing a therapeutic substance to a patient in need of the substance, establishing an electrical field which encompasses a predetermined region of tissue within the patient, exposing the tissue to the electrical field for a time and under conditions sufficient to permit the permeation of the substance across the cell membranes of cells located within the region of tissue, and contacting the tissue with at least one agent which is capable of prolonging the permeability of the cell membranes in the tissue exposed to the electrical field.

Use of the invention facilitates the transport of certain therapeutic substances to their site of action, inside the cell. Even under unfavorable conditions, such as low concentrations of therapeutic substance within the target tissue and substance with a large or irregularly shaped molecular structure, the present techniques can be effective in the delivery of therapeutic substances.

In one aspect, this invention provides a method for the concentration of therapeutic substances within a diseased region of tissue. Utilization of this technique improves the efficacy of electroporation mediated delivery while minimizing side effects associated with the administration of cytotoxic substances.

A further aspect of this invention provides a method for the use of substances capable of prolonging the permeabilized state of the cell membrane, dramatically improving the intracellular delivery of therapeutic substances.

DETAILED DESCRIPTION OF THE INVENTION

The present invention provides methods to facilitate the intracellular delivery of substances via electroporation. In particular, these methods can be applied to improve the benefit derived from the application of electroporation therapy to diseased tissue.

In one aspect, the invention provides a method for delivering a therapeutic substance to a predetermined location in a patient comprising providing a therapeutic substance to a patient in need of the substance, establishing an electrical field which encompasses a predetermined region of tissue within the patient, exposing the tissue to the electrical field for a time and under conditions sufficient to permit the permeation of the substance across the cell membranes of cells located within the region of tissue, and contacting the tissue with at least one agent which is capable of prolonging the permeability of the cell membranes in the tissue exposed to the electrical field.

The design of an efficient electroporation therapy must take into account numerous factors which can affect either the presence of therapeutic substance or propagation of the electric fields. The present invention discloses important aspects of an effective electroporation therapy, including: (1) concentration of therapeutic substance within the tissue, and (2) manipulation of the ensuing membrane permeability state. Methods are described which optimize these factors and thereby improve the overall effectiveness of electroporation therapy.

Figure 1:
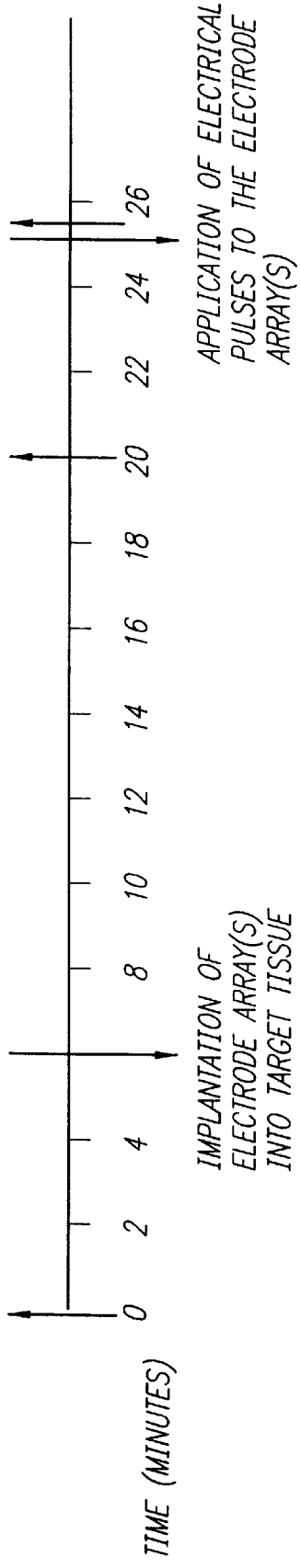
FIG. 1 is a graphical time line illustrating the temporal relationship of various elements of a typical electroporation therapy protocol.

FIG. 1 illustrates a representative time line for the individual elements comprising an effective electroporation therapy. Since the cells begin to resume normal function immediately following the application of the treatment, optimal therapeutic benefit is dependent on the action of the substances delivered into the cells. Therefore, these procedures and their specific sequence have been designed to maximize the concentration of therapeutic substance delivered to the intracellular space. While the precise timing of these procedures will depend in part on the specific application, optimal therapeutic benefit is dependent on maintaining the general temporal relationship described in FIG. 1.

Administration of Therapeutic Substances

Electroporation therapy has provided a means for the intracellular delivery of normally impermeant therapeutic substances in treated cells and tissue. By impermeant is meant that the substance does not permeate an intact cell membrane at a rate sufficient to allow meaningful equilibration between the extracellular and intracellular concentrations of the substance. Therapeutic substances will include those compositions which display at least one desirable pharmacological action in cells or tissue when administered to a patient. Typically, such substances will display their effects primarily when introduced intracellularly, and will include a broad range of substances including, without limitation, pharmacological compounds such as e.g. cytotoxic drugs, nucleic acids such as e.g. DNA, RNA, genes and antisense sequences, antibodies, and the like.

Careful consideration must be given to the methods for delivery of the therapeutic substance to the interstitial space of the target tissue. Each therapeutic substance will have individual characteristics, such as molecular size, charge, solubility, and shape which can effect its transport within a living organism, as well as across the membrane of a living cell. The route of administration can also dramatically effect the dosage and timing required for the effective delivery of therapeutic substances to a specific tissue system.

In order to overcome obstacles to the delivery of therapeutic substances to tumor tissue, direct injection to the area to be treated, e.g. intratumoral injections in the case of tumor therapy, have been employed as part of electroporation therapy. These injections can provide very high levels of therapeutic substance within the tumor with relatively few systemic side effects. While this technique has shown great promise, it does not always provide a complete solution to the problem of distribution. Injections directly into the tumor cannot always overcome the barriers which limit the dispersal of therapeutic substances throughout the tumor environment. This is especially true for therapeutic substances of large size or irregular shape.

In addition to the difficulty associated with homogeneous distribution of the substance, many solid tumors have advanced locally, creating an anaplastic region of diseased tissue which is not part of the main tumor mass. Small groups of "micrometastatic" cells reside in this area, and can result in tumor recurrence if left untreated. It would be very difficult to target these small groups of cells with direct injections of drug or therapeutic substance. However, since this region does not share the problematic anatomy of the main tumor mass, the use of vascular injections becomes more appealing. In addition, the intravascular administration of therapeutic substance will slow clearance of the intratumoral injection by decreasing the concentration gradient between the tumor tissue and the vasculature. Therefore, an optimized treatment of some solid tumors would utilize a combination of intratumoral and vascularly distributed therapeutic substance to be completely effective.

In order to achieve an optimal result, sufficient concentrations of the therapeutic substance must be distributed throughout the diseased region. The dosage and timing of the intravascular and intratumoral administrations will depend on the specific therapeutic substance and the characteristics of the targeted tissue. These administration parameters will be optimized to provide adequate levels of therapeutic substance throughout the target region at the time of pulsing.

Typically the intratumoral injection would be given first with time allotted for distribution of the therapeutic substance. After a time period deemed sufficient for adequate distribution of the substance, an intravascular injection can also be administered. The selected route of administration will depend on the specific therapeutic substance. For substances such as genes, which can experience substantial uptake by the liver (i.e. first pass effect), an intraarterial injection in the vessels leading to the targeted tissue can provide higher concentrations of therapeutic substance in the tissue. In the case of drugs, such as bleomycin, adequate concentrations can usually be achieved with an intravenous administration.

Timing of the electrical pulses in relation to the administration of the therapeutic substance is an important factor in the treatment of diseased tissue. If adequate time is not provided for the distribution of the therapeutic substance, significant portions of the targeted tissue may not derive therapeutic benefit from the treatment. Conversely, if the application of the electrical pulses is delayed too long, the levels of therapeutic substance in the target tissue may decrease below the levels sufficient to achieve the desired effect. The interval between therapeutic administration and application of the electrical pulses should be based on a pharmacokinetic analysis of the therapeutic substance with respect to the targeted tissue. This temporal relationship should be selected to maximize the therapeutic concentration in the interstitial space of the tissue at the time of pulsing.

In the case of bleomycin, pharmacokinetic studies have indicated a plasma elimination half life of approximately four hours. Bleomycin levels monitored in tumors after intravenous administration indicate a significant decrease in the intratumoral bleomycin concentration between 30 minutes and 120 minutes post injection. The peak concentration of bleomycin in tumor tissue depends greatly on the location and histological type of the tumor. For many tumors a 5 to 15 minute interval between injection and the application of electrical pulses is sufficient to achieve adequate levels of drug in the tissue.

The pharmacokinetics of the intratumoral bleomycin injection must also be considered when planning a treatment protocol. It has been determined that the peak plasma levels occur approximately 45 minutes after intramuscular injection of bleomycin. This indicates that bleomycin rapidly moves from tissue into the blood stream. The timing of the intratumoral bleomycin will be highly dependent on the type of tissue being injected. Since the central regions of a tumor are often hypovascular and necrotic there is little concern that drug levels will decrease too rapidly. Typically the intratumoral injection would be administered from approximately 15 to 25 minutes before the intravenous dose.

Delivery of Electroporation-Inducing Electrical Fields

Although not strictly an aspect of prolonging membrane permeability, it has been observed that an effective electroporation therapy will consist in part of the application of threshold level electric fields uniformly throughout a targeted region of tissue where sufficient concentrations of a therapeutic substance are present. An important aspect of this therapy is the delivery of the electrical pulses. The most commonly reported method for the delivery of these pulses is to utilize a small array of needle electrodes which penetrate the tissue to the desired depth. Coverage of the entire targeted area is accomplished by repositioning the array throughout the area and applying electrical pulses to each incremental region encompassed by the array. This method is deficient for several reasons. First, there can be mechanical damage to the tissue as a result of the penetrating needles, a problem which is exacerbated by the multiple placements. Some common complications are hemorrhaging from blood vessels and piercing of vital structures. The incidence of complications is related to the number of electrodes in the array and the total number of placements made. If a substantial number of placements are required to treat a targeted area, the risk of complications may become too great to justify the treatment. This drawback is of significant concern in highly vascular organs such as the brain, liver, pancreas, kidney, lung, and colon.

Figure 8A:
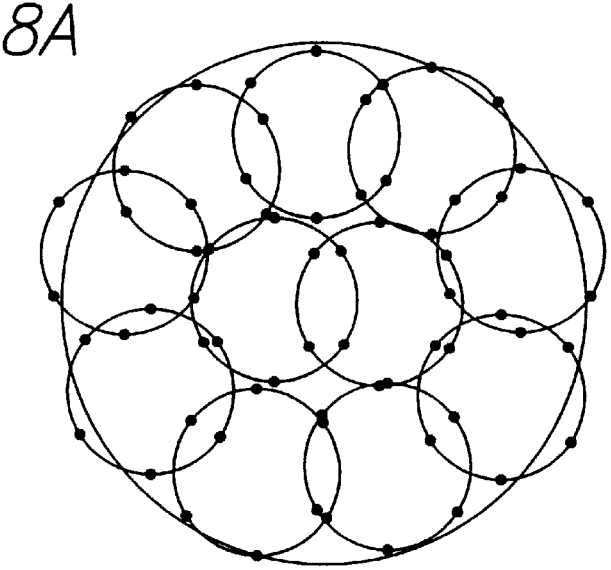
FIG. 8A is a diagram that illustrates the electrode placements required to effectively treat a 3.0 cm diameter region with a 1.0 cm diameter hexagonal electrode array.
Figure 8B:
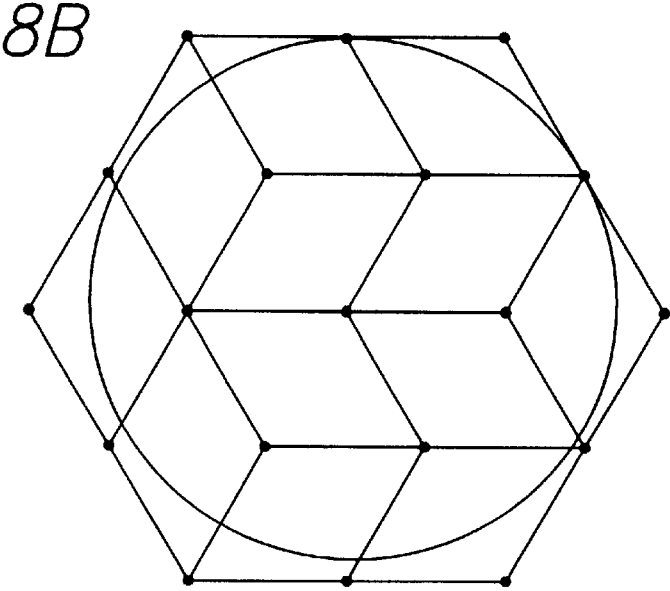
FIG. 8B depicts a larger electrode array capable of treating a 3.0 cm diameter region in a single placement.

Another disadvantage of electrode arrays requiring multiple placements is the difficulty associated with accurately treating the entire targeted area. As an organ or tissue is manipulated during treatment, it can be difficult to accurately assess the exact region treated by any given array placement. It becomes especially difficult for those electrode arrays in which the area of treatment is not defined exactly by the area of the electrodes. For example, in the case of a 1.0 cm diameter, six electrode, hexagonal array described in U.S. Pat. No. 5,702,359, it would be difficult to accurately apply pulses to a typical tumor area. A satisfactory treatment can only be achieved by treating the entire tumor area which includes a significant margin of normal tissue into which cancerous cells have begun to infiltrate. Often, the entire target area can have a diameter of 3.0 cm or more. In order to effectively treat such an area, the 1.0 cm diameter array would need to be separately placed at least ten times in an accurate fashion (see FIGS. 8A and 8B), assuming that little or no overlap is required to insure uniform treatment of the tissue. An analysis of the fields generated by this electrode array, as discussed in U.S. patent application Ser. No. 09/119,352, now abandoned, incorporated in its entirety herein by this reference, reveals that significant overlap in array placement is in fact desirable for complete coverage. Based on these data, it could require up to 16 array placements to ensure complete treatment of an area similar to the one illustrated in FIG. 8.

An analysis of this method of treatment reveals another difficulty associated with multiple placements of the array. Care must be taken during the penetration of the electrodes to avoid blood vessels and other vital structures as well as continue to efficiently and accurately treat the entire targeted region. This process requires a significant amount of time, during which the levels of therapeutic substance in the tissue are decreasing due to exchange with the blood stream. The rate of this transfer is dependent on the initial concentrations of the therapeutic substance as well as the vascular anatomy of the target tissue. Unless measures are taken to mitigate this problem, the amounts of time required to perform multiple electrode placements may yield a sub-optimal treatment due to decreased concentrations of therapeutic substance at the time of electrical pulsing.

This problem is also exacerbated if complications, such as bleeding, arise after an electrode placement. If circumstances dictate that the surgeon interrupt the therapy and treat the complications before proceeding, then further delay and a definite change in therapeutic substance concentration results.

An alternate method of treatment can be employed to avoid many of these difficulties. An array designed to cover the target tissue region with a single placement would provide an accurate method of treating large volumes of tissue. This would mitigate any concerns of decreasing levels of therapeutic present within the tissue. Since the electrical pulses would be applied to the entire target region within a close temporal relationship, any complications could be dealt with after the pulses have been delivered and the electrode arrays removed. U.S. patent application Ser. Nos. 08/476,714, now U.S. Pat. No. 6,041,252, 08/845,553, now U.S. Pat. No. 5,873,849, and 09/119,352, now abandoned, the entire contents of which are incorporated by reference herein, disclose electrode arrays capable of treating large volumes of tissue in a single placement.

After the placement of an electrode array around the target tissue and a period of time sufficient for distribution of the therapeutic substance, the electrical pulses can be applied to the tissue. Electroporation pulses applied to tissue typically have an amplitude of 100 to 3000 V, a duration of approximately 1 to 1000 μsec, and a pulse frequency on the order of 1 Hz. The electrical pulses should be applied in a fashion such that uniform electric fields are generated throughout the targeted tissue. It is also desirable to propagate these fields in multiple directions in order to increase the likelihood that the entire target tissue will be effectively treated. Such an activation pattern requires a sequencing device capable of independently addressing the electrodes within an array.

Improvements in field uniformity can be derived from the simultaneous activation of more than two electrodes. By applying the electric pulses in this fashion the inefficient "fringe effects" characteristic of two electrode systems can be reduced. However, the simultaneous activation of additional electrodes increases the number of parallel pathways, leading to a reduction in the equivalent resistance of the "circuit" (i.e. an increase in the electrical load seen by the pulse generator). Therefore, an adequate pulse generator must meet the power requirements necessary for applying pulses to such low resistance loads.

Figure 9:
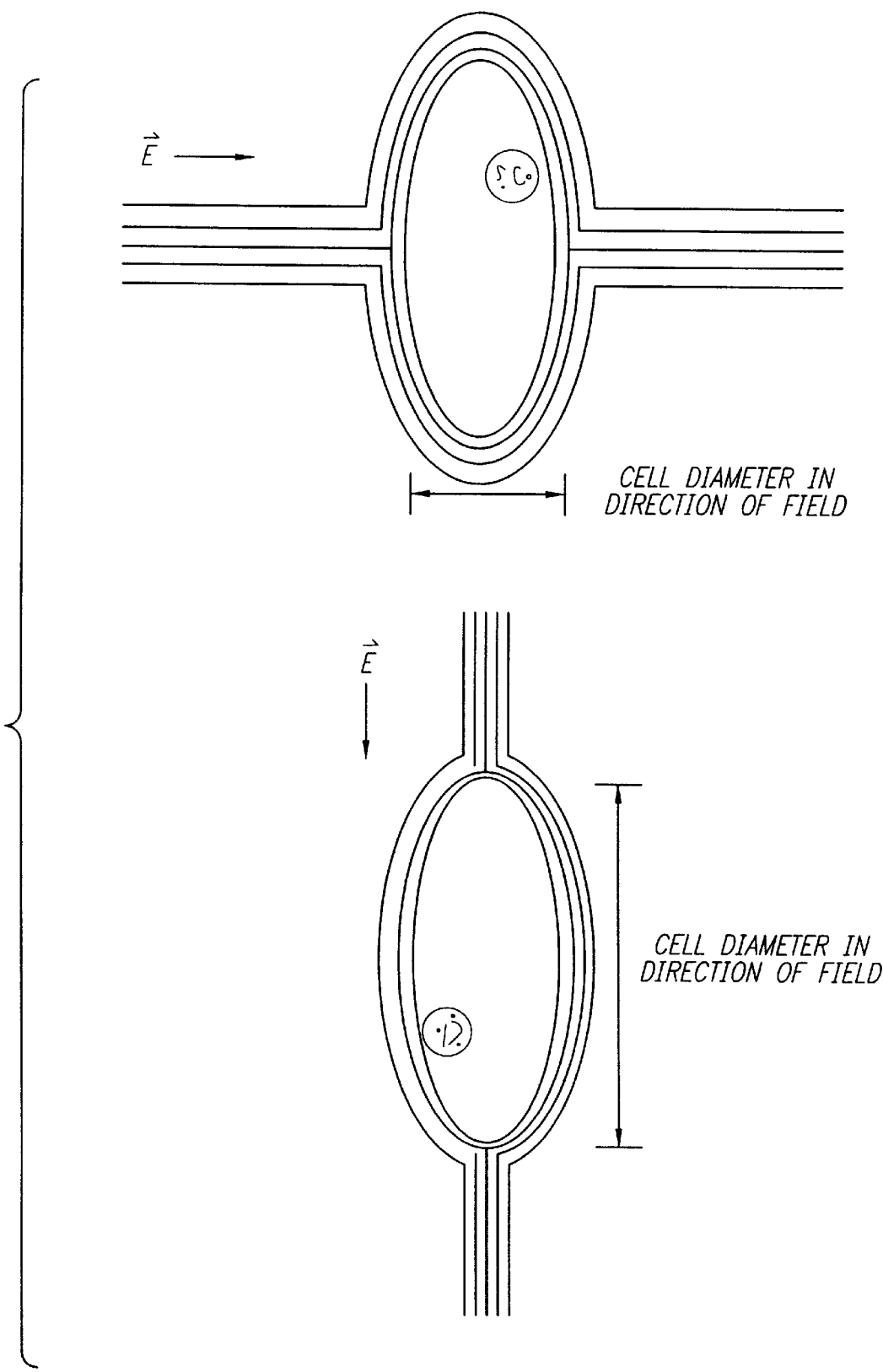
FIG. 9 is a diagram illustrating the effect of electric field orientation on cell membrane permeability, wherein given an equivalent electric field E, the voltage generated across the cell membrane will be proportional to the diameter of the cell in the direction of the electric field.

Application of the electric fields at more than one angle can improve the probability that any given segment of the target tissue is permeabilized. Due to the irregular shapes characteristic of cells in tissue, there are often preferential orientations at which the cell will be more efficiently permeabilized. Effective electroporation of a cell requires that a threshold voltage (on the order of 1 V) be established across the cell membrane before membrane permeability will occur. As FIG. 9 illustrates, the angle at which the electric field is propagated can effect the voltage established across an individual cell membrane. The voltage established across the membrane is proportional to the cell diameter in the direction of the electric field, therefore the physical dimensions of the cell can significantly alter the electric field strength (and therefore the applied voltage) required to permeabilize the cell. Since there are limits to the voltages that can safely be applied to tissue, a more practical method for maximizing the probability of membrane permeability is to propagate the electric fields at several different angles. This approach increases the likelihood that the fields will be applied in a favorable orientation and result in membrane permeability.

By altering the electrical state of selected electrodes in relationship to others in the array, the electric fields can be applied in several different directions. This method of pulsing can be accomplished by utilizing independently addressed electrodes connected to suitable switching means. Desirably the switching sequence could be preprogrammed and controlled by a digital processor. However, mechanical switching means could also be made effective for given applications.

Prolonging Cell Membrane Permeability

In vitro studies have demonstrated that the efficiency of electroporation mediated delivery is strongly correlated to the cell temperature at which the electrical pulses are delivered. At high temperatures, membrane permeability is achieved with relatively low applied voltages. However, the duration of the permeabilized state is dramatically reduced. This is believed to be due to the increase in membrane fluidity observed at higher temperatures (above 25° C.). Since the cell membranes are more fluid, reorganization occurs much faster, resulting in a shorter pore duration. As the temperature is reduced, the cell membranes are much less fluid and require slightly higher applied voltages to achieve membrane permeability, however, a subsequent increase in pore duration is observed.

Since diffusion of the therapeutic substance across a permeabilized membrane is a time dependent process, extending the duration of the permeability state increases transmembrane delivery of the substance. If the duration of the permeability state were extended sufficiently, a greater equilibration between the extracellular and intracellular concentrations would be observed. While the duration of the permeability state in an in vitro situation can easily be manipulated by lowering the temperature, this is not easily accomplished when electroporation therapy is applied in the treatment of living tissue.

It has been determined that a wide variety of exogenous agents can affect the function of cell membranes. When cells are exposed to such agents, properties such as membrane fluidity can be significantly altered. Since temperature-induced decreases in membrane fluidity increased the efficiency of electroporation-mediated delivery of substances in vitro, it was concluded that exposure to membrane stabilizing agents may provide substantial benefit to electroporation for tissue applications. By exposing cells to such agents directly after the electrical pulses have been delivered, a transient stabilization of the cell membrane in the permeable state could be achieved, allowing more prolonged diffusion of the therapeutic substance across the cell membrane, and more complete equilibration of the extracellular and intracellular concentrations.

There are many agents which are known to cause significant decreases in membrane fluidity. While the steroids are the most prevalent class of agents known to induce this characteristic effect, several other classes of compounds can be utilized in a similar fashion as well.

Figure 2:
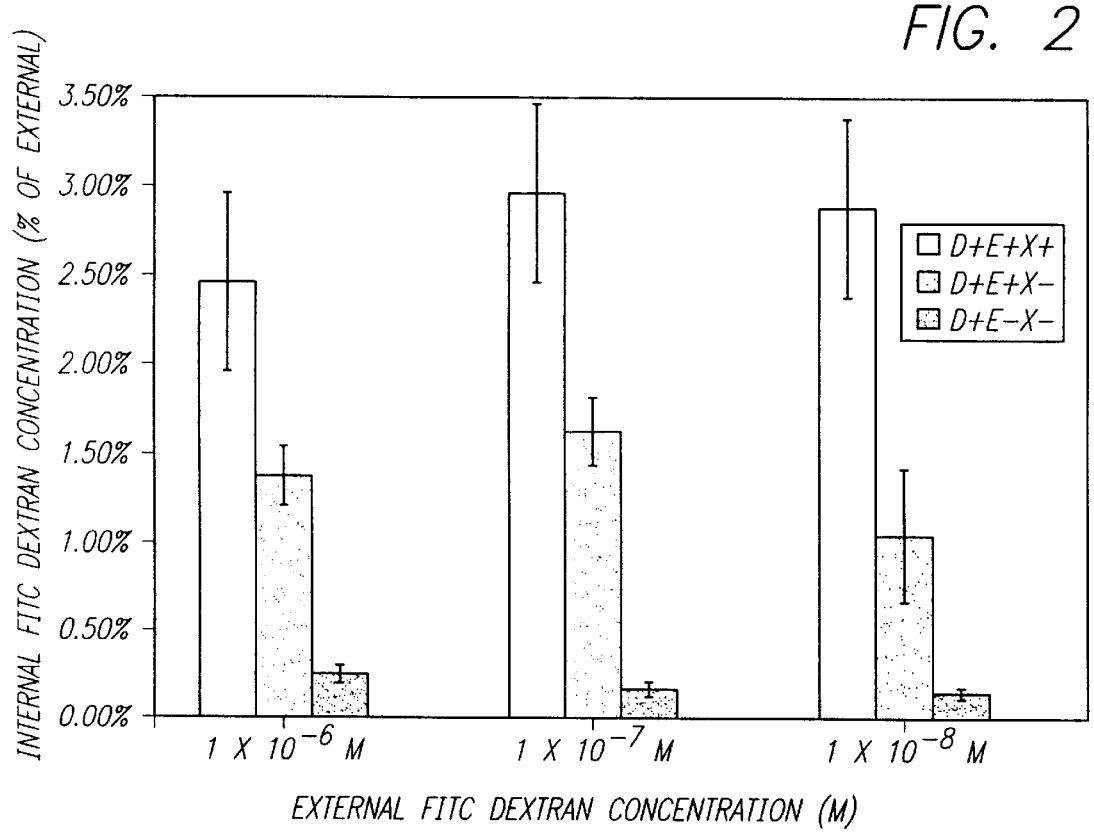
FIG. 2 is a bar graph illustrating the loading of a marker substance for the experiment described in Example 2.

Studies of the effects of dexamethasone have determined that cells exposed to this corticosteroid exhibit a significant decrease in membrane fluidity. Based upon this property, dexamethasone and other steroids are utilized in order to obtain the desired benefits in electroporation therapy. For example, in vitro and in vivo studies of dexamethasone indicate that use of the steroid in conjunction with electroporation substantially improves the therapeutic effect derived from the treatment. FIG. 2 illustrates the results of an in vitro study measuring the delivery of fluorescein isothiocyanate-labeled Dextran (FITC-Dextran) of 40,000 weight average molecular weight. As can be seen, a significant increase in intracellular FITC-Dextran is observed for 9L gliosarcoma cells exposed to electric pulses followed immediately by dexamethasone when compared to cells exposed only to the electric fields.

Figure 3:
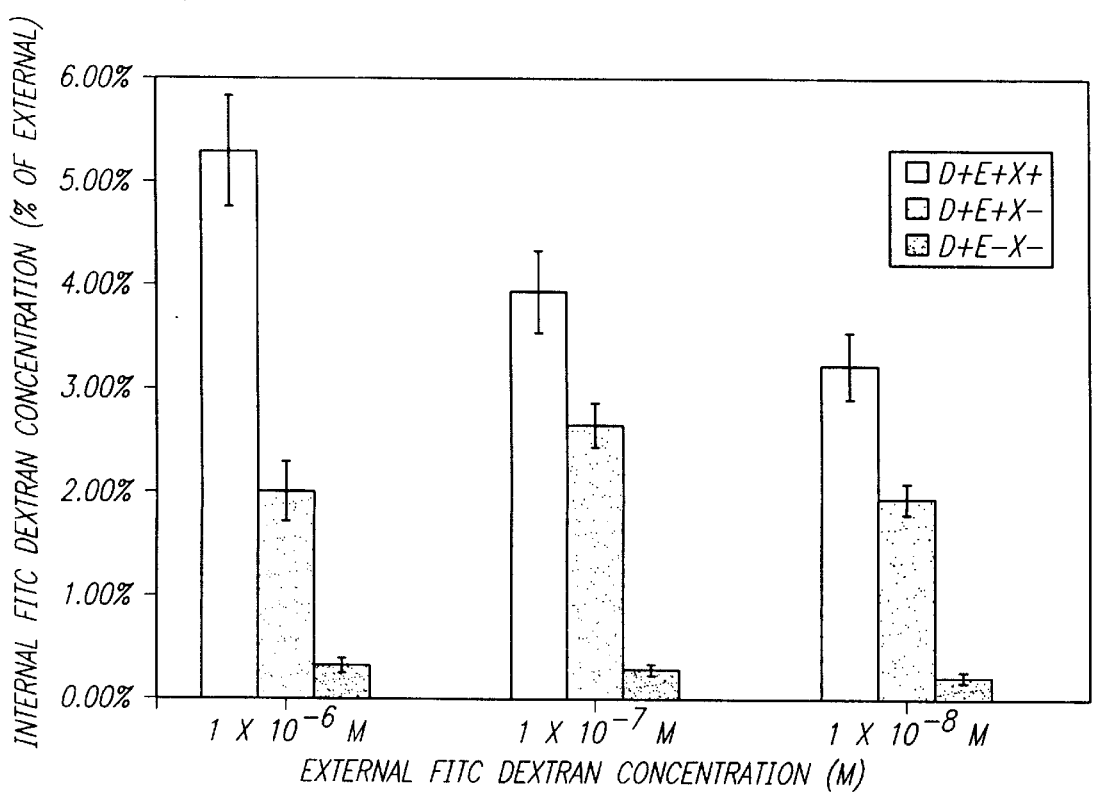
FIG. 3 is a bar graph illustrating the loading of a marker substance for the experiment described in Example 3.

A similar effect is observed when the human Panc-1 cell line is treated under similar conditions. FIG. 3 illustrates the increased intracellular concentration of FITC-Dextran achieved in the Panc-1 cells exposed to electrical pulses immediately followed by the administration of dexamethasone. It can therefore be concluded that the benefit derived from dexamethasone is not confined to a single cell type and could be useful for many different applications.

Figure 4:
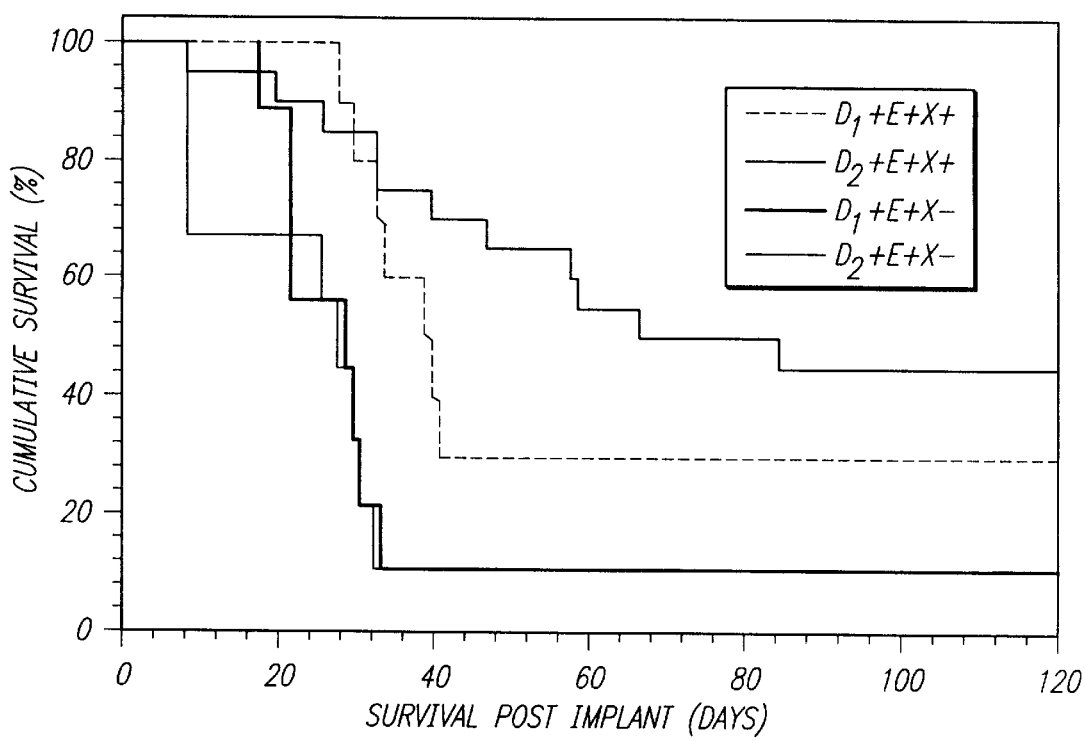
FIG. 4 is a Kaplan-Meier survival chart of the results for the experiment described in Example 5.

In vivo studies using a 9L brain tumor implanted in Fischer rats demonstrate a substantial increase in therapeutic benefit derived from the use of dexamethasone immediately after an electroporation therapy consisting of a bleomycin dose followed by electrical pulses (see FIG. 4). Control studies (FIG. 5) demonstrate that the effect of dexamethasone is related to the electrical pulsing and that it does not provide any therapeutic benefit when administered without all elements of the therapy. As FIG. 6 illustrates, a substantial improvement in therapeutic benefit was derived only when dexamethasone is administered immediately after the electrical pulsing. The therapeutic benefit observed in groups where dexamethasone is administered at other time points does not differ from that of animals that receive the electroporation treatment without dexamethasone.

Based on these results, it can be concluded that the use of dexamethasone can significantly improve electroporation as a method for the intracellular loading of therapeutic substances. The temporal relationship between the dexamethasone and the electrical pulsing lends support to the hypothesis of a stabilization of the membrane permeability. Since the use of dexamethasone is clinically acceptable, this procedure offers a feasible method for the enhancement of the electroporation effect. In order to derive the greatest benefit from the use of dexamethasone, it should be injected intravascularly immediately following the application of the electrical pulses. Since the benefit of dexamethasone is derived from increasing the duration of the membrane permeability state, it must be administered before a substantial number of the membranes have begun to recover from the pulsing. The electrode array system described in the previous section provides an efficient method of applying the electrical pulses, thus permeabilizing cell membranes within the entire target region in a close temporal relationship. These procedures minimize the amount of membrane recovery occurring before the dexamethasone can be administered. The proper dosage of dexamethasone to be used in conjunction with electroporation therapy is dependent on the specific application. For human patients receiving electroporation therapy with bleomycin for the treatment of a malignant tumor, a single dose of dexamethasone, approximately 0.1 milligram per kilogram of body weight, should be sufficient to achieve a beneficial effect.

Other substances which have a mode of action similar to that of dexamethasone would also be expected to produce similar results when used in the same fashion. Examples of such agents include other steroids such as prednisone, methylprednisolone, and progesterone. Other agents such as Angiotensin II and Vitamin E can act to decrease membrane fluidity and would also be candidates for use with electroporation therapy in the practice of the present invention. When methylprednisolone is tested in a fashion similar to the methods used with dexamethasone, there is some improvement derived, although to a lesser extent than the benefit provided by dexamethasone (see FIG. 7). Although the improved efficiency provided by methylprednisolone is not as dramatic as that of dexamethasone these results indicate that more than one substance can enhance the effect of electroporation by prolonging membrane permeability.

The following examples serve to illustrate certain preferred embodiments and aspects of the present invention and are not to be construed as limiting the scope thereof.

Experimental

In the experimental disclosure which follows, all weights are given in grams (g), milligrams (mg), micrograms ($\mu$g), nanograms (ng), or picograms (pg), all amounts are given in moles (mol), millimoles (mmol), micromoles ($\mu$mol), nanomoles (nmol), picomoles (pmol), or femtomoles (fmol), all concentrations are given as percent by volume (%), proportion by volume (v:v), molar (M), millimolar (mM), micromolar ($\mu$M), nanomolar (nM), picomolar (pM), femtomolar (fM), or normal (N), all liquid volumes are given in liters (L), milliliters (mL), or microliters ($\mu$L), all solid volumes are given in cubic centimeters (cc), and linear measurements are given in millimeters (mm), micrometers ($\mu$m), or nanometers (nm), unless otherwise indicated. The following examples demonstrate the practice of the present invention in enhancing electroporation mediated transmembrane delivery of therapeutic substances.

EXAMPLE 1

In vitro Assay for the Quantification of Intracellular FITC-Dextran

In this Example, an in vitro assay is provided for the quantitative determination of intracellular FITC-Dextran, in order to demonstrate the benefits derived from the practice of the present invention.

Cells grown in culture are harvested according to the standard procedures for the specific cell line. After the harvest procedure, the cells are suspended at a standard density in Dulbecco's Modified Eagle Media.

A 0.7 mL aliquot of the cell suspension is then placed in a 4 mm electroporation cuvette, together with a 0.1 mL volume of FITC-Dextran solution (FD-40, Sigma Chemicals, St. Louis, Mo.). After a 5 minute exposure to the fluorescent labeled compound, the cuvette is placed into the electroporation chamber of a Cytopulse PA-2000 square wave generator. Six electroporation pulses of amplitude 600 Volts and duration 80 $\mu$sec are applied to the cuvette.

Immediately following the pulses a 0.2 mL volume of FITC-Dextran at a concentration identical to that of the original suspension is transferred into the cuvette. After 15 minutes of exposure, the cell suspension is spun in a centrifuge at 6000 rpm for 5 minutes. The supernatant is removed and the cells washed in phosphate buffered saline (PBS). This procedure is repeated three more times to remove any extracellular FITC-Dextran from the solution.

The cells are then counted with a hemocytometer and resuspended at a known density. Three mL of the suspension is then transferred into a quartz cuvette and placed into a Turner Designs TD700 fluorimeter (Turner Designs, Sunnyvale, Calif.) for an evaluation of the fluorescent label. After the initial fluorescence reading 0.1 mL of an anti-FITC monoclonal antibody (Molecular Probes Inc., Eugene, Oreg.) is placed into the cuvette to quench any extracellular FITC-Dextran that was not washed out. The cuvette is again placed into the TD700 fluorimeter and a reading taken. The readings can then be compared to the results obtained for other groups as well as FITC-Dextran standard solutions.

EXAMPLE 2

In vitro Electroporation of the 9L Gliosarcoma Cell Line

In this Example, in vitro tests are performed generally according to the procedure outlined in Example 1 to demonstrate the effect of dexamethasone on electroporation efficiency in the 9L gliosarcoma cell line.

After the cell harvesting procedure, the cells are suspended at a density of $2.15 \times 10^6$ cells/mL. For each of the groups being tested, 0.7 mL of the cell suspension is added to a cuvette in addition to a 0.1 mL solution of FITC-Dextran. Tests are performed at three different FITC-Dextran concentrations: $1 \times 10^{-6}$M, $1 \times 10^{-7}$M, and $1 \times 10^{-8}$M.

Four different groups are employed during this example. Cells are exposed to one of the following regimens (where D=Dextran, E=Electrical Pulsing, and X=Dexamethasone): Harvest and washing procedure alone ($D^{31}$ $E^-$ $X^-$), FITC-Dextran alone ($D^+$ $E^-$ $X^-$), FITC-Dextran and electrical pulsing ($D^+$ $E^+$ $X^-$) or all three experimental elements ($D^+$ $E^+$ $X^+$). Immediately after the electrical pulses are delivered 0.2 mL of a solution is added to the cuvette: For the ($D^+$ $E^+$ $X^-$) groups, this solution consists of PBS and FITC-Dextran at a concentration identical to the original solution in the cuvette. For the ($D^+$ $E^+$ $X^+$) groups, the solution consists of $2 \times 10^{-5}$M dexamethasone and the concentration matched FITC-Dextran.

After the washing procedure, $4 \times 10^5$ cells are suspended in PBS and placed into an optical quartz cuvette. Readings are recorded for the groups before and after the addition of the anti-FITC antibody. Readings for the ($D^-$ $E^-$ $X^-$) group are used to establish a zero level for intracellular FITC-Dextran. Although no FITC-Dextran is added to the ($D^-$ $E^-$ $X^-$) groups, readings for these groups indicate the presence of low level background noise. The procedure is repeated six times for each experimental group.

FIG. 2 illustrates the results for this Example, where each of the groups tested are represented on the x axis and the y axis indicates the approximate intracellular concentration of FITC-Dextran measured in the cells of each group as a percentage of the extracellular concentration at the time of pulsing. This quantity is determined by measuring the overall fluorescence of each sample and comparing it to standard concentrations of FITC-Dextran. The concentration standards are formulated based on the intracellular volume of the 9L gliosarcoma cell. By comparing the experimental samples to the concentration standards, an approximate intracellular FITC-Dextran concentration can be determined. This intracellular concentration is then divided by the extracellular concentration present at the time of pulsing.

It is apparent that significantly more FITC-Dextran is present in cells exposed to the electrical pulses ($D^+$ $E^+$ $X^-$) than the group which received no pulses ($D^+$ $E^-$ $X^-$). A significant increase in FITC-Dextran loading is also observed when dexamethasone is added immediately after the pulsing ($D^+$ $E^+$ $X^+$) when compared to cells that received the electrical pulsing, but no dexamethasone ($D^+$ $E^+$ $X^-$). This result indicates that dexamethasone can act to further potentiate the electroporation effect, resulting in a higher intracellular concentration of FITC-Dextran.

EXAMPLE 3
In vitro Electroporation of Human Panc-1 Cells

This Example repeats the procedure described in Example 2 to demonstrate that the effect observed in the 9L gliosarcoma cell line can also be observed in the human Panc-1 cell line.

The experiments are performed generally according to the procedure outlined in Example 1. After harvesting, the Panc-1 cells are suspended at a density of $4.3 \times 10^5$ cells/mL. An 0.7 mL aliquot of this suspension is added to each 4 mm cuvette. Five minutes before pulsing a 0.1 mL solution of FITC-Dextran is added to the cuvette. Three concentrations of FITC-Dextran are tested during these experiments, $1 \times 10^{-6}$M, $1 \times 10^{-7}$M, and $1 \times 10^{-8}$M.

Four groups (($D^-$ $E^-$ $X^-$), ($D^+$ $E^-$ $X^-$), ($D^+$ $E^+$ $X^-$), ($D^+$ $E^+$ $X^+$)), identical to those described in the previous Example are tested. The ($D^+$ $E^+$ $X^+$) group is exposed to $2 \times 10^{-5}$M dexamethasone immediately following the electrical pulse regimen.

After the 15 minute exposure time and the washing procedure described in Example 1 are performed, the cells are suspended at a density of $3.3 \times 10^4$ cells/mL. Three mL of the suspension are placed in an optical quartz cuvette and the reading is recorded from the TD700 fluorimeter. A 0.1 mL volume of the anti-FITC antibody is then added to quench any extracellular FITC-Dextran and another reading is recorded. The entire procedure is repeated six times for each experimental group.

The results of the experiments described in this Example are illustrated in FIG. 3, where the x axis indicates the groups tested at each FITC-Dextran concentration and the y axis represents the approximate intracellular concentration in the Panc-1 cells as a percentage of the extracellular concentration at the time of pulsing. These values can be directly compared to those provided in FIG. 2 for the testing performed in Example 2.

As can be seen from FIG. 3, the Panc-1 cell line responds similarly to the 9L cell line, in that a dramatic increase in intracellular FITC-Dextran is observed when electrical pulses are applied to the cell suspension. Also, the addition of dexamethasone after the pulses provides an additional increase in FITC-Dextran loading into the cells.

EXAMPLE 4
Tumor Model Used in Survival Studies

The experimental brain tumor model employed in the following examples is the 9L gliosarcoma in the female Fischer rat.

Tumor implants consist of 200,000 9L gliosarcoma cells suspended in 2.3 μL of Dulbecco's Phosphate Buffered Saline. After anesthetization by intraperitoneal injection of a ketamine/xylazine mixture, the scalp is shaved and swabbed with Betadine® solution. After placement in a stereotaxic apparatus, a 1 cm incision is made in the scalp above bregma. A burr hole is drilled in the skull 1 mm anterior and 3 mm lateral of bregma. The injection needle is lowered stereotactically 4 mm deep, into the right caudate nucleus. After slow injection of the cells (4 minutes for 2.3 μL), the needle is raised and the burr hole sealed with bone wax. After careful irrigation of the area, the wound is closed with surgical staples.

EXAMPLE 5
Role of Dexamethasone

Forty animals undergo the tumor implantation procedure described in Example 4 and are assigned to one of four experimental groups in order to demonstrate that dexamethasone has an effect on the in vivo efficiency of electroporation. Treatments consist of a bleomycin injection followed 30 minutes later by the delivery of a series of electric pulses to the implanted tumor. These pulses are intended to permeabilize the membranes of the exposed cells, significantly increasing the uptake of bleomycin into the cells. Experimental subjects receive treatments consisting of either electroporation treatment alone ($D^+$ $E^+$ $X^-$) or in combination with a single dose of steroid immediately following the treatment ($D^+$ $E^+$ $X^+$). Each of the treatment protocols are tested in the presence of two different concentrations of bleomycin.

On the eighth day post implantation (tumor mass approximately 0.02 cc), the rats are anesthetized with an i.p. injection of a ketamine/xylazine mixture. After placement in the stereotaxic apparatus, the scalp is disinfected with Betadine®. Another incision is made in the scalp and the burr hole located. An electrode array comprising three elongate rod electrodes oriented in an approximate equilateral triangle is placed in the stereotactic arm. The array is placed around the burr hole so that each electrode is approximately equidistant from the implant hole. New burr holes are drilled to accommodate the electrodes. The array is then lowered with the stereotaxic arm to a depth of 5 mm.

The femoral vein of the animal is then exposed and the bleomycin injected intravenously over approximately fifteen seconds. Animals receive either 1 unit per kg body weight (($D_1^+$ $E^+$ $X^-$), ($D_1^+$ $E^+$ $X^+$)) or 2 units per kg body weight (($D_2^+$ $E^+$ $X^-$), ($D_2^+$ $E^+$ $X^+$)) depending on the group. After 30 minutes to allow circulation of the bleomycin, the animals are exposed to a regimen of brief high voltage pulses. Each pulse has an amplitude of 450 volts (1 kV/cm based on the established electrode spacing) and a duration of 100 $\mu$sec. Four pulses are applied at each of the three single-primary-two secondary electrode combinations. After completion of the pulse regimen, the animals in the ($X^+$) groups are injected intravenously with a 0.5 mg/kg dose of the steroid dexamethasone. Finally, the electrode array is slowly extracted, the burr holes sealed with bone wax, and the incision sealed with surgical staples. The animals can then be placed in a heated recovery area.

FIG. 4 provides a Kaplan-Meier survival chart illustrating the outcome of the four experimental groups, where the x-axis represents days of survival after tumor implantation and the y-axis represents the percentage of subjects alive on a given day. There is a statistically significant difference ($P<0.01$, Rank Sum Test) in survival between groups, at either bleomycin concentration, that received a steroid injection ($D_{1,2}^+$ $E^+$ $X^+$) and those that did not ($D_{1,2}^+$ $E^+$ $X^-$). As FIG. 4 illustrates, in the absence of the agent prolonging the permeability of the cell membrane, there was no detectable improvement in intracellular concentration of the therapeutic substance when the extracellular concentration was increased. However, the agent was employed there was a noticeable benefit from when a higher drug dosage was given.

EXAMPLE 6

Dexamethasone Controls

In order to demonstrate that the effect observed in Example 1 is not due to the interaction of dexamethasone with any of the individual components of the treatment control groups are tested. Fifty animals are implanted with tumors according to the procedure outlined in Example 4. Each animal is assigned to one of three control groups. The first group of ten animals ($D^+$ $E^-$ $X^+$) is prepared according to the procedure outlined in Example 5. Each subject receives a 2 mg/kg intravenous injection of bleomycin. However, after the thirty minute circulation time no electrical pulses are administered to the animal. Each animal then receives a single 0.5 mg/kg intravenous dose of dexamethasone.

The second group of ten animals ($D^-$ $E^+$ $X^+$) is prepared according to the procedure outlined in Example 5, however, no bleomycin is administered to the subjects. The treatment proceeds according to the procedure outlined in Example 5 with a 0.5 mg/kg dexamethasone injection immediately following the pulse regimen. The final group of 30 animals receive no form of treatment ($D^-$ $E^-$ $X^-$)

Figure 5:
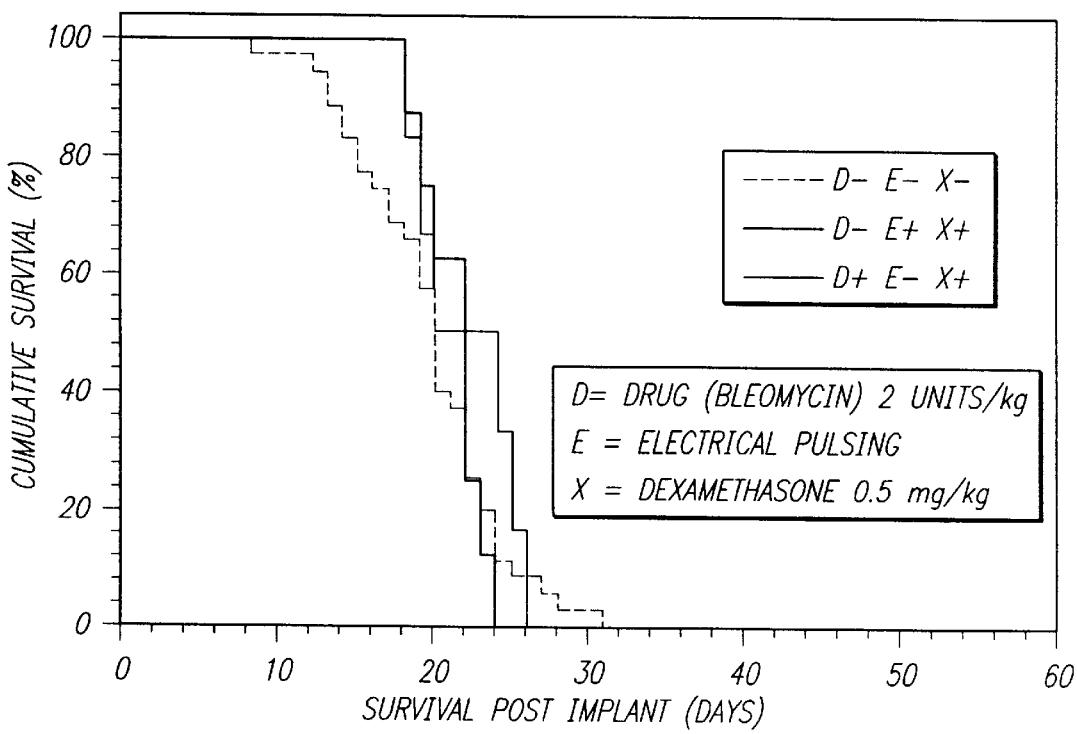
FIG. 5 is a Kaplan-Meier survival chart of the results for the experiment described in Example 6.
Figure 6:
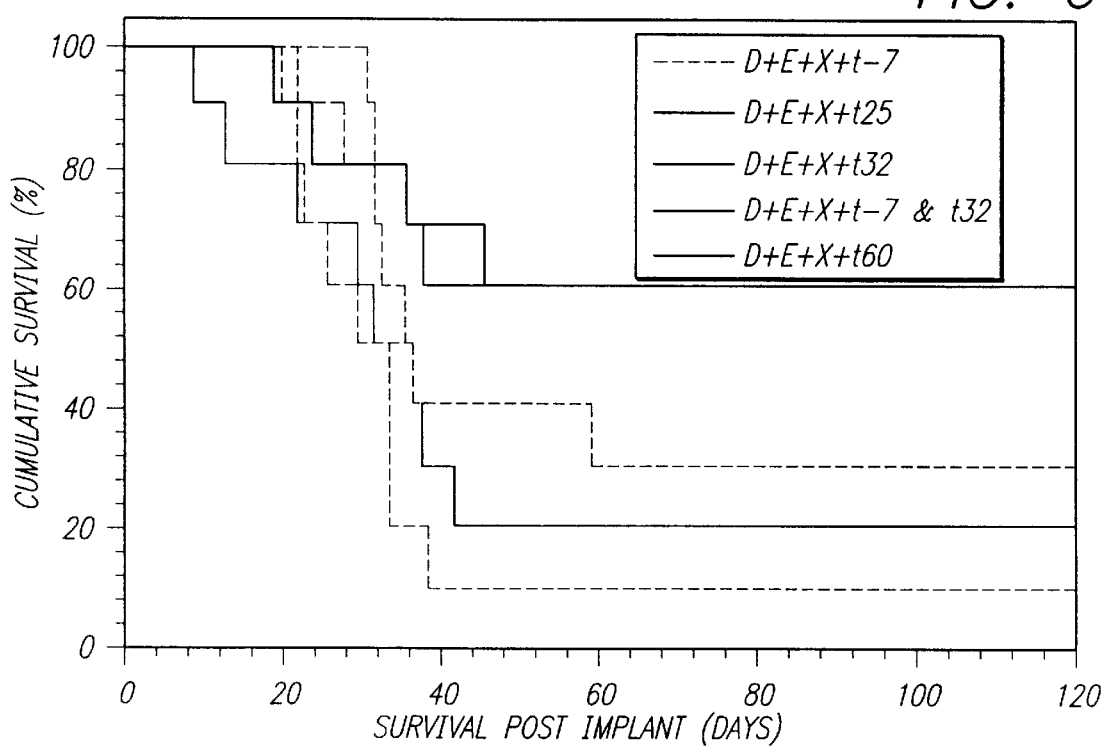
FIG. 6 is a Kaplan-Meier survival chart of the results for the experiment described in Example 7.

In FIG. 5 a Kaplan Meier chart illustrates the outcome of the control groups. The x-axis represents days of survival after tumor implantation and the y-axis represents the percentage of subjects alive on a given day. As can be seen in the figure, no therapeutic benefit is observed for animals that received bleomycin and dexamethasone ($D^+$ $E^-$ $X^+$) or pulsing and dexamethasone ($D^-$ $E^+$ $X^+$). There is no significant difference in survival between any of the control groups. It can therefore be concluded that the effect of dexamethasone observed in Example 5 is related to the use of electroporation.

EXAMPLE 7

Importance of Timing in the Use of Dexamethasone

In order to demonstrate the temporal nature of the effect of dexamethasone, fifty animals implanted with tumors according to the procedure outlined in Example 4 are assigned to five groups. The treatment of each group is identical except for the timing of the 0.5 mg/kg intravenous dexamethasone injection. The timing of the five groups is as follows: 1. 7 minutes before the injection of bleomycin ($t_{-7}$), 2. 25 minutes after the injection of bleomycin ($t_{25}$), 3. Immediately following the electrical pulse protocol ($t_{32}$), 4. 30 minutes after the pulse protocol ($t_{60}$), and 5. ½ dose (0.25 mg/kg) 7 minutes before the injection of bleomycin and a FULL dose immediately following the electrical pulse protocol ($t_{-7\&32}$). The timing designations are based on a protocol in which bleomycin injection occurs at time $t_0$ and the electrical pulse protocol is initiated 30 minutes later at time $t_{30}$.

On the eighth day post implantation (tumor mass approximately 0.02 cc), the rats are prepared for treatment in a manner consistent with the description in Example 5, except that dexamethasone injections are given according to the schedule above and have been excluded from this description. The femoral vein of the animal is exposed and 2 units/kg body weight of bleomycin is injected intravenously over approximately fifteen seconds. After 30 minutes to allow for circulation of the bleomycin, the animals are exposed to a regimen of brief high voltage electrical pulses. Each pulse has an amplitude of 450 volts (1 kV/cm based on the established electrode spacing) and a duration of 100 $\mu$s. Four pulses are applied at each of three single-primary-two secondary electrode combinations. Finally, the electrode array is slowly extracted, the burr holes sealed with bone wax, and the incision sealed with surgical staples. The animals can then be placed in a heated recovery area.

FIG. 6 provides a Kaplan-Meier survival chart illustrating the results for the five experimental groups. The x-axis represents days of survival after tumor implantation and the y-axis represents the percentage of subjects alive on a given day. From FIG. 6 it can be seen that 60% (12 of 20) animals that receive a dexamethasone injection immediately following the electroporation pulses ($t_{32}$, $t_{-7\&32}$) survived 120 days with no evidence of tumor recurrence. In comparison, animals that receive a dexamethasone injection at any other time ($t_{-7}$, $t_{25}$, $t_{60}$) had a combined 120 day survival rate of only 20% (6 of 30). Statistically significant differences in survival exist between $t_{32}$ and $t_{25}$ ($P<0.02$, Rank Sum Test), $t_{32}$ and $t_{60}$ ($p=0.05$), and also between $t_{-7\&32}$ and $t_{25}$ ($P<0.04$). When groups are combined, a statistically significant difference in survival exists between the administration of dexamethasone immediately after pulsing and at any other time ($P<0.01$).

These results demonstrate that the significant advantages in therapeutic effect conferred by the administration of dexamethasone have a limited window of applicability, and are related to the effects of the electroporation pulses.

EXAMPLE 8

In vitro Use of Methylprednisolone with the 9L Gliosarcoma Cell Line

In vitro tests are performed to demonstrate that the steroid methylprednisolone has an effect similar to that of dexamethasone on the electroporation efficiency in the 9L gliosarcoma cell line. These experiments are performed according to the procedure outlined in Example 1.

After the cell harvesting procedure, the cells are suspended at a density of $2.15 \times 10^6$ cells/mL. For each of the groups being tested, 0.7 mL of the cell suspension is added to a cuvette in addition to a 0.1 mL solution of FITC-Dextran. Tests are performed at two different FITC-Dextran concentrations, $1 \times 10^{-6}$M and $1 \times 10^{-7}$M. Only the ($D^+$ $E^+$ $M^+$) (Methylprednisolone) group is tested during these experiments; results for the ($D^+$ $E^-$ $M^-$) and ($D^+$ $E^+$ $M^-$) groups are taken from the testing described in Example 2.

Immediately after the electrical pulses are delivered, a 0.2 mL solution is added to the cuvette. For the ($D^+$ $E^+$ $M^+$) groups, the 0.2 mL solution consists of $2 \times 10^{-5}$M Methylprednisolone and the concentration matched FITC-Dextran.

After the washing procedure, $4 \times 10^5$ cells are suspended in PBS and placed into an optical quartz cuvette. Readings are recorded for the groups before and after the addition of the anti-FITC antibody.

Figure 7:
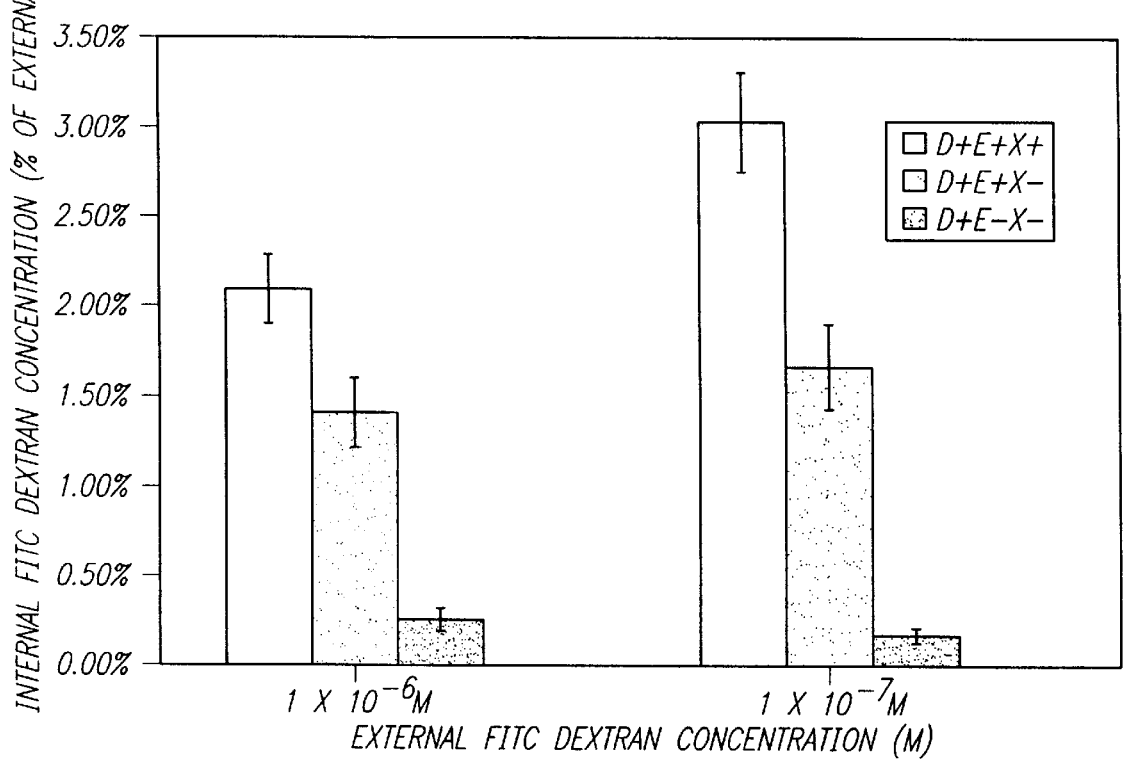
FIG. 7 is a bar graph illustrating the loading of a marker substance for the experiment described in Example 8.

FIG. 7 depicts the results for this experiment, where each of the groups tested are represented on the x axis, and the y axis indicates the approximate intracellular concentration of FITC-Dextran measured in the cells of each group as a percentage of the extracellular concentration present at the time of pulsing. This quantity is determined by measuring the overall fluorescence of each sample and comparing it to standard concentrations of FITC-Dextran. The concentration standards are formulated based on the intracellular volume of the 9L gliosarcoma cell. By comparing the experimental samples to the concentration standards an approximate intracellular FITC-Dextran concentration can be determined.

It is apparent that there is a benefit derived from the use of Methylprednisolone in conjunction with electroporation, although the magnitude is not as significant as that observed with dexamethasone. The performance of methylprednisolone as an agent could be improved by optimizing the dosage level in the cuvette. However, this result demonstrates that compounds other than dexamethasone can act to further potentiate the electroporation effect, resulting in a higher intracellular concentration of FITC-Dextran, or other substances such as therapeutic substances.

All patents and patent applications cited in this specification are hereby incorporated by reference as if they had been specifically and individually indicated to be incorporated by reference.

Although the foregoing invention has been described in some detail by way of illustration and example for purposes of clarity and understanding, it will be apparent to those of ordinary skill in the art in light of the disclosure that certain changes and modifications may be made thereto without departing from the spirit or scope of the appended claims.

What is claimed is:

1. A method for delivering a therapeutic substance to a region of tissue in a patient comprising:
   providing a therapeutic substance to a patient in need of said substance;
   establishing an electrical field which encompasses a region of tissue within said patient;
   exposing said region of tissue to said electrical field for a time and under conditions sufficient to permit the permeation of said substance across the cell membranes of cells located within said region of tissue; and
   administering to said patient at least one agent which is capable of prolonging the permeability of the cell membranes in the tissue exposed to said electrical field in a manner so that said agent does not contact said region of tissue until after the tissue's exposure to the electrical field.

2. A method for delivering a therapeutic substance as recited in claim 1 wherein said agent comprises at least one compound which temporarily decreases cell membrane fluidity.

3. A method for delivering a therapeutic substance as recited in claim 2 wherein said agent comprises a steroid.

4. A method for delivering a therapeutic substance as recited in claim 2 wherein said agent comprises at least one member selected from the group consisting of dexamethasone, prednisone, methylprednisolone, progesterone, Angiotensin II and Vitamin E.

5. A method for delivering a therapeutic substance as recited in claim 2 wherein said agent comprises at least dexamethasone.

6. A method for delivering a therapeutic substance as recited in claim 1 wherein said therapeutic substance is provided to the patient by direct administration to the region of tissue within said patient.

7. A method for delivering a therapeutic substance as recited in claim 1 wherein said therapeutic substance is provided to the patient by systemic administration to the patient.

8. A method for delivering a therapeutic substance as recited in claim 1 wherein said therapeutic substance is provided to the patient by a combination of systemic administration to the patient and direct administration to the region of tissue within said patient.

9. In a method for delivering a therapeutic substance to a region of tissue located in a patient wherein said tissue has been exposed to an electroporation-inducing electrical field, the improvement comprising:
   contacting said tissue after it has been exposed to said electrical field with at least one agent which is capable of prolonging the permeability of the cell membranes in the tissue exposed to said electrical field.

10. A method for delivering a therapeutic substance as recited in claim 9 wherein said agent comprises at least one compound which temporarily decreases cell membrane fluidity.

11. A method for delivering a therapeutic substance as recited in claim 10 wherein said agent comprises a steroid.

12. A method for delivering a therapeutic substance as recited in claim 10 wherein said agent comprises at least one member selected from the group consisting of dexamethasone, prednisone, methylprednisolone, progesterone, Angiotensin II and Vitamin E.

13. A method for delivering a therapeutic substance as recited in claim 10 wherein said agent comprises at least dexamethasone.

14. A method for delivering a therapeutic substance as recited in claim 9 wherein said therapeutic substance is provided to the patient by direct administration to the region of tissue within said patient.

15. A method for delivering a therapeutic substance as recited in claim 9 wherein said therapeutic substance is provided to the patient by systemic administration to the patient.

16. A method for delivering a therapeutic substance as recited in claim 9 wherein said therapeutic substance is provided to the patient by a combination of systemic administration to the patient and direct administration to the region of tissue within said patient.

* * * * *